(12) United States Patent
Ortlieb

(10) Patent No.: US 6,708,991 B1
(45) Date of Patent: Mar. 23, 2004

(54) AMBULATORY IV DOLLY

(76) Inventor: Art Ortlieb, 1338 S. 202 Second St., Eagle, NE (US) 75206

(*) Notice: Subject to any disclaimer, the term of this patent is extended or adjusted under 35 U.S.C. 154(b) by 0 days.

(21) Appl. No.: 10/188,820

(22) Filed: Jul. 5, 2002

(51) Int. Cl.$^7$ ................................................ B62B 1/10
(52) U.S. Cl. ........................... 280/47.26; 280/47.33; 280/79.2; 248/122.1; 248/125.1
(58) Field of Search .................... 280/35, 47.12, 280/47.131, 47.17, 47.18, 47.19, 47.24, 47.26, 47.33, 79.2; 604/80, 259; 24/127, 128; 248/129, 122.1, 125.1, 125.8, 126, 121

(56) References Cited

U.S. PATENT DOCUMENTS

| | | | | |
|---|---|---|---|---|
| 3,168,329 | A | * | 2/1965 | Goldschmidt ................ 280/651 |
| 3,804,432 | A | * | 4/1974 | Lehrman ..................... 280/654 |
| 4,266,765 | A | * | 5/1981 | Sandoval et al. ............. 482/68 |
| 4,807,837 | A | | 2/1989 | Gawlik |
| 4,832,294 | A | * | 5/1989 | Eidem ...................... 248/125.8 |
| 4,893,824 | A | * | 1/1990 | Turek et al. ............. 280/47.27 |
| 4,905,944 | A | * | 3/1990 | Jost et al. ................. 248/125.8 |
| D310,570 | S | * | 9/1990 | Wells ........................ D24/128 |
| 5,114,023 | A | * | 5/1992 | Lavin ........................ 211/107 |
| 5,337,992 | A | | 8/1994 | Pryor |
| 5,479,953 | A | * | 1/1996 | Pasulka ....................... 135/66 |
| 5,489,109 | A | * | 2/1996 | Murphy .................... 280/415.1 |
| D385,348 | S | | 10/1997 | Ward |
| 5,700,257 | A | | 12/1997 | Minick |
| 5,857,685 | A | | 1/1999 | Phillips |
| 5,890,687 | A | * | 4/1999 | Pryor et al. ................ 248/158 |
| 6,056,249 | A | | 5/2000 | Fillon, Jr. |
| 6,224,072 | B1 | * | 5/2001 | Weck et al. ............. 280/47.35 |
| 6,390,311 | B1 | * | 5/2002 | Belokin ...................... 211/204 |

* cited by examiner

*Primary Examiner*—Frank Vanaman
*Assistant Examiner*—Brian C Swenson
(74) *Attorney, Agent, or Firm*—Randal D. Homburg

(57) ABSTRACT

An ambulatory cart to carry an IV pump, the IV bags or bottles and other items associated with portable IV units, the ambulatory cart having a light-weight plastic basket to which is attached two wheel for rolling the cart, the basket having a front leg to maintain the ambulatory cart in an upright level position when the ambulatory cart is at rest and a bumper at the rear to absorb impact when pulling the cart up stairs or steps. The ambulatory cart also includes two vertical support bars with a handle at the top of the bars, the support bars having an adjustable bracket with at least one bottle securing strap. Also attaching to the adjustable bracket and the handle is an adjustable height support staff having a horizontal IV bottle hanging support. The adjustable bracket slides and attaches vertically on the support bars to adjust to a height to provide IV bags or bottles with secure support, while the support staff slides vertically and attaches to the handle and the adjustable bracket.

2 Claims, 2 Drawing Sheets

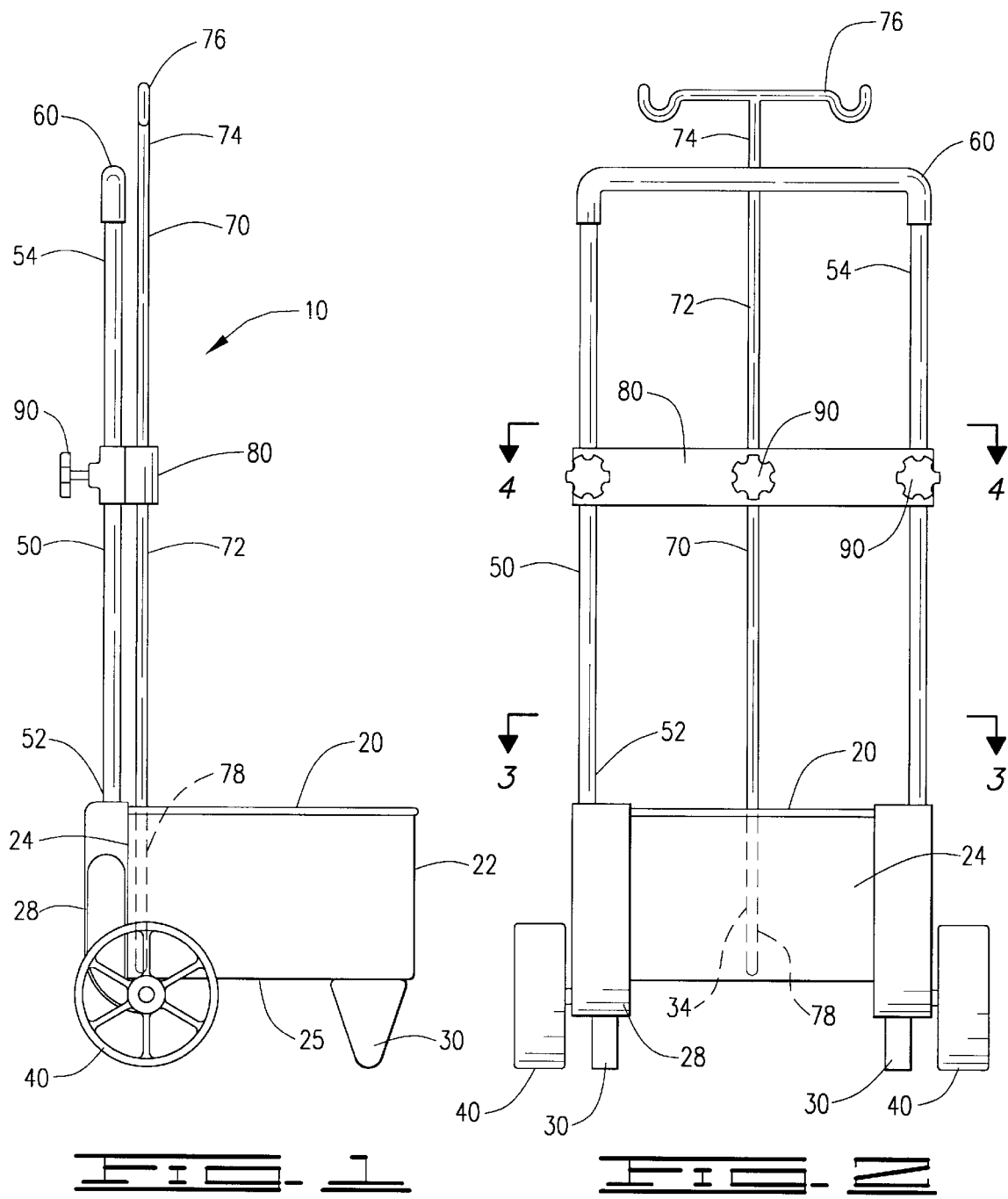

AMBULATORY IV DOLLY

CROSS REFERENCE TO RELATED APPLICATIONS

None

I. BACKGROUND OF THE INVENTION

1. Field of Invention

The invention is an ambulatory cart to carry an IV pump, the IV bags or bottles and other items associated with portable IV units, the ambulatory cart having a light-weight plastic basket to which is attached two wheel for rolling the cart, the basket having a front leg to maintain the ambulatory cart in an upright level position when the ambulatory cart is at rest and a bumper at the rear to absorb impact when pulling the cart up stairs or steps. The ambulatory cart also includes two vertical support bars with a handle at the top of the bars, the support bars having an adjustable bracket with at least one bottle securing strap. Also attaching to the adjustable bracket and the handle is an adjustable height support staff having a horizontal IV bottle hanging support. The adjustable bracket slides and attaches vertically on the support bars to adjust to a height to provide IV bags or bottles with secure support, while the support staff slides vertically and attaches to the handle and the adjustable bracket.

2. Description of Prior Art

The following United States patents were discovered and are disclosed within this application for utility patent. All relate to IV devices for transporting an IV system. A first patent, U.S. Pat. No. 5,700,257 to Minick, discloses a pouch within which is contained an IV bag and small ambulatory pump, the pouch having closure flaps to secure the IV bag and pump within the pouch.

A non-wheeled three leg support stand for suspending a plurality of IV bags is disclosed in U.S. Pat. No. 4,807,837 to Gawlik. A design patent illustrating a four-wheeled mounted infusion pump stand is disclosed in U.S. Design Pat. No. D 385,348 to Ward, comprising a singular vertical pole.

A portable IV support pole is disclosed in U.S. Pat. No. 6,056,249 to Fillon, Jr., wherein the single vertical pole has two adjustable vertical members which swivel independent of each other to prevent the tangling of the IV lines during transport of the portable IV support pole. This patent has no basket. U.S. Pat. No. 5,337,992 to Pryor discloses a portable IV support stand handle having a large grip portion, the handle attaching to an IV support stand with the handle resting on the telescoping adjustment portion of a singular vertical member, the handle also having screw to attach to the bottom of accessories having screw holes. This handle also has a channel to accept a headboard or footboard of a bed.

A improvement to a hospital cart is disclosed in U.S. Pat. No. 5,857,685 to Phillips which includes a common wheeled cart having a lower shelf and an upper shelf, with three adjustment receivers located in the top shelf, each receiver accepting an IV pole with the three adjustment receivers oriented in a triangle to promote stability of the cart.

II. SUMMARY OF THE INVENTION

The primary objective of the invention is to provide a portable cart to allow a patient on an IV to carry his IV accessories and infusion pumps with him, providing stable and secure transport of the IV accessories and giving the patient enhanced mobility.

A second objective of the invention is to provide a device similar to a dolly, which may be tilted onto two wheels having a basket to contain an IV infusion pump at a lowered location giving the device a lower center of gravity, preventing accidental overturning of the IV transport device, the device seeking an upright orientation due to the low center of gravity, while securing potentially breakable glass IV bottles.

A third objective is to provide the invention in an embodiment to allow for the easy transport of the device up steps or stairs, unlike the prior art, which must be transported on a flat surface only.

III. DESCRIPTION OF THE DRAWINGS

The following drawings are submitted with this utility patent application.

FIG. 1 is a side view of the dolly.

FIG. 2 is a rear view of the dolly basket.

IV. DESCRIPTION OF THE PREFERRED EMBODIMENT

Figure 3:
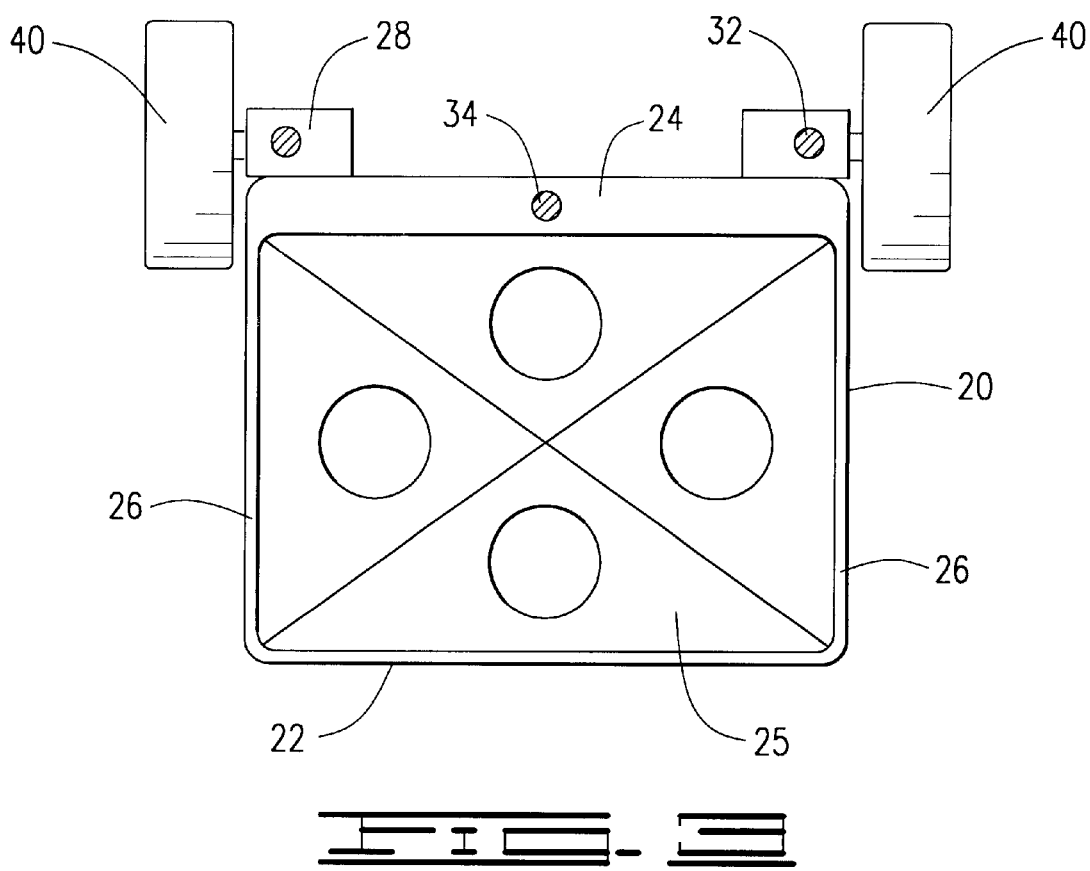
FIG. 3 is an upper view of the dolly basket.

The invention, as shown in FIGS. 1–4 of the drawings, is an ambulatory IV transport device 10 allowing a patient, requiring an IV with an IV infusion pump, enhanced secure mobility during ambulation, the device 10 comprising essentially a light weight basket 20 to which is attached two vertical support rods 50 having an upper handle 60 between the two vertical support rods 50 at the respective upper ends 54 of the support rods 50, two wheels 40, an adjustable slide bracket 80 engaging the support rods 50, and a central vertical IV suspension post 70 adjustably attaching to the adjustable slide bracket 80 to suspend IV bags and bottles, the IV bags and bottles secured to the adjustable slide bracket 80, with the basket 20 receiving an infusion pump and other IV accessories.

Figure 4:
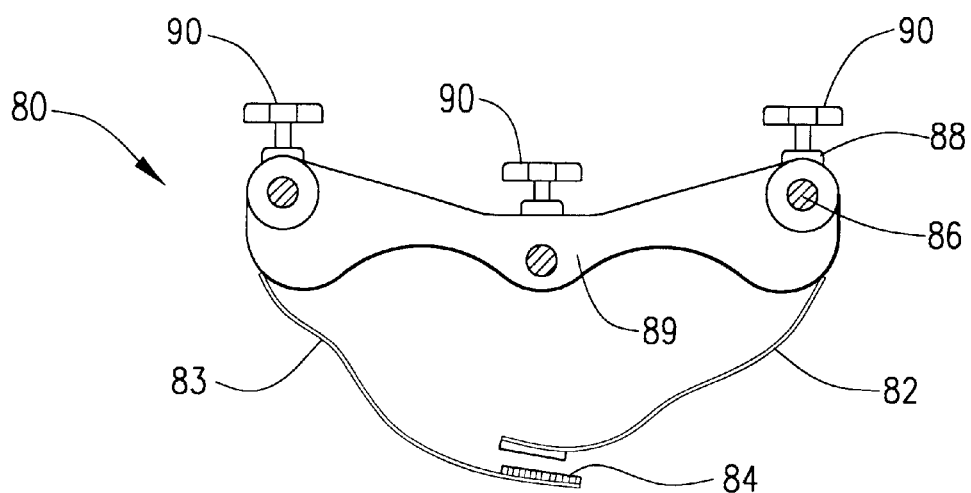
FIG. 4 is an upper view of the adjustable slide bracket.

The ambulatory IV transport device 10, more specifically comprises the light-weight basket 20, shown in FIGS. 1,2 and 4 of the drawings, having a front panel 22, a rear panel 24, bottom panel 25 and two side panels 26, at least one resilient bumper 28 attached to the rear panel 24, with at least one front basket rest 30 extending below the bottom panel 25 near the front panel, two attached wheels 40 extending laterally from the rear panel 24, and two internally threaded support rod receivers 32 located at the junction of the side panels 26 and rear panel 24 meet, each internally threaded support rod receiver 32 accepting a threaded lower end 52 of each of the two vertical support rods 50, each of the vertical support rods 50 also including the upper ends 54, to which the upper handle 60 is affixed, the upper handle 60 connecting the upper end 54 of the two vertical support rods 50 together. The vertical support rods 50 also support the adjustable slide bracket 80, slidably engaging the two vertical support rods 50 between the upper end 54 and the lower end 54 of each vertical support rod 50.

The adjustable slide bracket 80, as shown in FIG. 3 of the drawings, has a bottle securing band 82, two vertical support rod channels 86 and two threaded fastening knobs 90, the fastening knobs 90 penetrating two internally thread knob receivers 88 into the support rod channels 86, each fastening knob 90 engaging the vertical support rods 50 which insert through the support rod channels 86, to lockingly position the adjustable slide bracket 80 at a chosen location on the vertical support rods 50. In addition, the adjustable slide bracket 80 has a center bracket 89 having a third fastening knob 90, the center bracket 89 supporting a shaft 72 of the central vertical IV suspension post 70, the shaft 72 having an upper end 74 having at least one perpendicular IV suspension hook 76, and a lower end 78 received within an IV suspension post bracket 34, the IV suspension post bracket 34 located on the rear panel 24 of the basket 20, as shown in FIG. 1 of the drawings.

The basket 20, most preferably, is made of a resilient plastic, and be of a size sufficient to contain an IV infusion pump and other accessories utilized in IV patients. The bottle securing band 82, shown in FIG. 3 of the drawings, most preferably is provided by two elastic band segments 83, each segment 83 attaching near the each of the vertical support rod channels 86 on the adjustable slide bracket 80, the two segments attaching to each other by an attachments means 84, which can be hook and loop fastening material. The resilient bumper 28, as shown in FIGS. 1–3 of the drawings, may be provided as a resilient loop extending from the rear panel 24 of the basket 20, this resilient bumper 28 providing protection to the basket 20 when going up stairs or steps, the resilient bumper 28 absorbing any impact, providing the device with the ability to be taken up or down stairs or steps.

The device 10 may be adjusted to hang and secure a variety of different sized IV bottles or IV bags at a selected height, the height adjustment made either by raising the IV suspension post 70, or by raising the adjustable slide bracket 80.

While the invention has been particularly shown and described with reference to a preferred embodiment thereof, it will be understood by those skilled in the art that changes in form and detail may be made therein without departing from the spirit and scope of the invention.

What is claimed is:

1. An ambulatory IV transport device allowing a patient who requires an IV with an IV infusion pump, enhanced secure mobility, the device comprising:

a light-weight basket having a front panel, a rear panel, bottom panel and two side panels;

at least one resilient bumper attached to the rear panel;

at least one front basket rest extending below the bottom panel;

two attached wheels extending from the rear panel;

two internally threaded support rod receivers, each internally threaded support rod receiver accepting a threaded lower end of each of two vertical support rods, each of said vertical support rods also including upper ends;

an upper handle affixed to the upper ends of the two vertical support rods connecting the two vertical support rods;

an adjustable slide bracket having two vertical support rod channels, slidably engaging the two vertical support rods between the upper end and the lower end of each vertical support rod, the adjustable slide bracket further including;

a bottle securing band and two threaded fastening knobs, the fastening knobs penetrating two internally threaded knob receivers into the support rod channels, each fastening knob engaging the vertical support rods inserting through the support rod channels, lockingly positioning the adjustable slide bracket on the vertical support rods; and a center bracket having a third fastening knob, the center bracket slidingly engaging a central vertical IV suspension post having a shaft having an upper end from which at least one perpendicular IV suspension hook extends, the shaft also having a lower end received within an IV suspension post bracket located on the rear panel of the basket.

2. The device, as disclosed in claim 1, wherein:

the basket is a resilient plastic and of a size sufficient to contain at least an IV infusion pump, the bottle securing band is provided by two elastic band segments, one segment attaching near the vertical support rod channels on the adjustable slide bracket, the two segments attaching to each other by an attachments means; and the resilient bumper is a resilient loop extending from the rear panel of the basket, the resilient bumper providing protection to the basket when going up stairs or steps, absorbing any impact and providing the device with the ability to be taken up or down stairs or steps.

* * * * *